US00PP10643P

United States Patent [19]

Gebelle et al.

[11] Patent Number: Plant 10,643

[45] Date of Patent: Oct. 13, 1998

[54] *PICEA PUNGENS*, GEBELLE

[75] Inventors: Anthony Gebelle, deceased, late of Huron, Ohio, by Anna M. Gebelle, executrix; Anna M. Gebelle; David J. Gebelle, both of 826 River Rd., Huron, Ohio 44839

[73] Assignees: Anna M. Gebelle; David J. Gebelle, both of Huron, Ohio

[21] Appl. No.: 785,925

[22] Filed: Jan. 21, 1997

[51] Int. Cl.[6] ..... A01N 5/00

[52] U.S. Cl. ..... Plt./50.1

[58] Field of Search ..... Plt./50.1

[56] References Cited

U.S. PATENT DOCUMENTS

P.P. 5,457 4/1985 Holden ..... Plt./50.1

*Primary Examiner*—James R. Feyrer
*Assistant Examiner*—Kent L. Bell
*Attorney, Agent, or Firm*—Chernoff, Vilhauer, McClung & Stenzel

[57] ABSTRACT

A new *Picea pungens* variety discovered as a chance seedling in a field of *Picea pungens* seedlings, has brilliant yellow new growth, that hardens to green with a blue tint four to six weeks later, which makes the variety a superb specimen plant for landscape use.

2 Drawing Sheets

BACKGROUND AND SUMMARY OF THE INVENTION

The present invention relates to a new and distinctive variety of the Picea family and more specifically to a plant of the *Picea pungens genera*, named 'Gebelle'.

This plant was discovered by Tony and Ann Gebelle in a cultivated area at Gebelle Nursery, 826 River Road, Huron, Ohio, in a block of *Picea pungens* seedlings in May 1971.

This particular variety's unique feature is its brilliant yellow growth in the spring. This uniform conical shaped plant remains golden yellow for approximately four to six weeks, until the new growth hardens to green with a blue tint.

In 1985, in order to determine the plant's merits, asexual reproduction of this new conifer through grafting was done by David J. Gebelle. The two grafted conifers have the same color characteristics as the parent plant. Custom grafts were made in 1989 and each year thereafter to the present year. These plants also have the same color characteristics and grow true to form.

DETAILED DESCRIPTION OF THE PLANT

Figure 1:
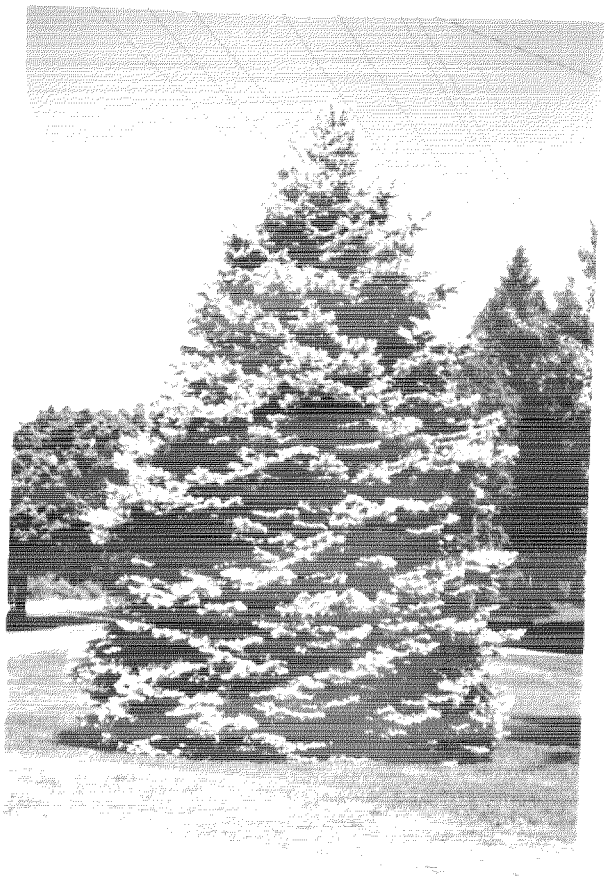
FIG. 1 shows the new variety in the spring displaying its brilliant yellow new growth.
Figure 2:
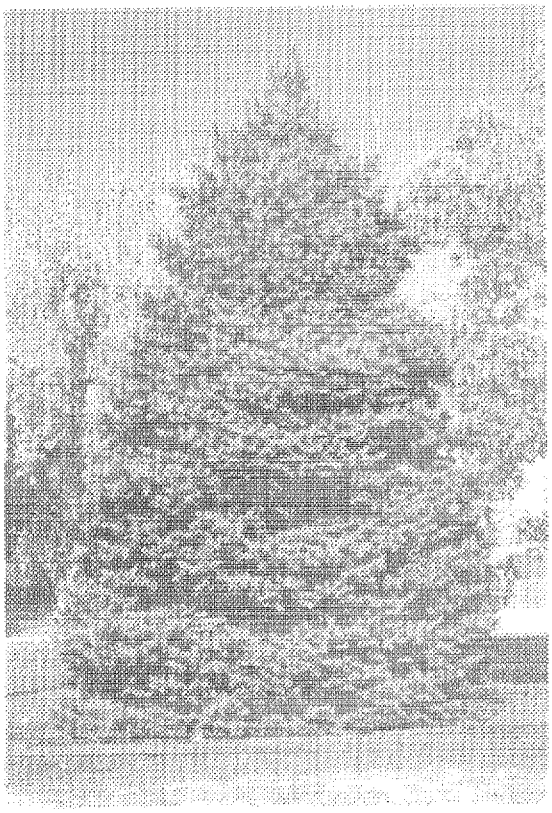
FIG. 2 shows the new variety in the summer when the new growth has hardened to green with a blue tint.

The following is a detailed description of this new and distinctive evergreen. To help in the identification of the colors the *Naturalist's Color Guide* by Frank B. Smithe, obtainable from the American Museum of Natural History, has been followed. Munsell notations of color are shown in parentheses. Observations were made from May through August 1996 at Huron, Ohio.

Buds

The buds which form on shoots of the previous year are Color 57—Sulfur Yellow (Munsell notation is 7.5 Y 8.0/6.0) and are approximately ⅛ inch (0.4 cm) long. The terminal bud grows about 5–8 inches (12.6–20.2 cm) a year. The lateral bud is smaller and grows about 4–5 inches (10.2–12.6 cm) per year. The oval shaped bud has scales which curve away from the bud.

Foliage

New growth is dense in whorls. Spruce needles are arranged in compact spirals around the twigs. The new needles are Color 157—Sulfur Yellow (Munsell notation is 7.8 Y 8.9/9.0) progressing to Color 55—Spectrum Yellow (Munsell notation is 6.0 Y 8.5/12.0) a distance of 9 to 14 cm. from the terminal. After approximately four to six weeks the new growth hardens to Color 163—Emerald Green (Munsell notation is 2.0 G 5.7/7.9) with a tint of Color 164—Cyan (Munsell notation is 5.3 GB 5.7/10.4).

Branch and Twig

Branches are thick and horizontal nearly at a right angle to the trunk. The twigs or woody projections are 4–5 inches (10.2–12.6 cm) long and the internode spacing ranges from 2–2.5 inches (5–6.4 cm) long. The needles occur singly on these projections or twigs. The tree is slow to self-prune lower branches, which gives it a dense appearance. The twigs are uniformly Color 139—True Cinnamon (Munsell notation 5.3 YR 5.3/5.4).

Size Characteristics

At 30 years, plant is 25 feet in height. Ultimate height is estimated to be 50 to 60 feet at 75 years. The subject variety is a compact grower with moderate shaping. Easily grown in most any soil conditions.

Leaves (Needles), Fruit

Their twigs are covered with leaves or needles, that grow closely together. Short needles are sharply pointed. Each needle is four sided, nearly square in cross-section. The needles vary 1.5 to 3.5 cm in length, spirally arranged, they extend outward from all sides of the branches.

Cones

The cones are scarce on the tree. Only a few cones have set over the years. The cones are 2.5 inches (6.4 cm) long and cylindrical ¾ inch (1.9 cm) across with thin, flexible scales. The cones are Color 139—True Cinnamon (Munsell notation is 5.3 YR 5.3/5.4) and fall late in the year. The cones mature in one season.

Texture

Twigs have soft needles with a slight sharpness to the tip.

Bark

The bark is 0.75 to 1.5 inches (1.9–3.8 cm) thick. The bark is rough with scaly ridges. Somewhat pale gray Color 119—Drab Gray (Munsell notation is 0.1 Y 6.8/2.1) then turns reddish brown Color 239—Ground Cinnamon (Munsell notation is 8.7 YR 5.2/3.6) and furrowed with age.

Growth Habit

The variety grows straight and tall tapering upward to a point. New growth on the original specimen radiates in whorls.

Hardiness

The variety is extremely hardy in an open, exposed location—USDA Zone 3. It has withstood temperatures above 100 degrees and as low as −25° F. without burning or scorching.

It is claimed:

1. A new distinctive and unique variety of *Picea pungens* tree, substantially as herein shown and illustrated, found in a block of *Picea pungens* seedlings, characterized by its brilliant yellow new growth which deepens to a golden yellow for about 4 to 6 weeks, and then hardens green with a blue tint.

* * * * *

UNITED STATES PATENT AND TRADEMARK OFFICE

CERTIFICATE OF CORRECTION

PATENT NO : PP10643

DATED : 10/13/98

INVENTOR(S): Anne Gebelle, Tony Gebelle, David Gebelle

It is certified that error appears in the above-identified patent and that said Letters Patent is hereby corrected as shown below:

Col. 4, 3rd line under "Hardiness" heading delete [.] after "25F"

Signed and Sealed this

Seventh Day of March, 2000

*Attest:*

*Attesting Officer*

Q. TODD DICKINSON

*Commissioner of Patents and Trademarks*